United States Patent
Steinmueller et al.

(10) Patent No.: US 8,005,629 B2
(45) Date of Patent: Aug. 23, 2011

(54) METHOD FOR MONITORING SENSOR FUNCTION

(75) Inventors: Dirk Steinmueller, Karlsruhe (DE); Wilfried Hammelehle, Korntal-Münchingen (DE); Detlev Wittmer, Maulbronn (DE); Axel Fikus, Hartha (DE)

(73) Assignee: Endress+Hauser Conducta Gesellschaft Für Mess-u. Regeltechnik mbH+Co. KG, Gerlingen (DE)

( * ) Notice: Subject to any disclaimer, the term of this patent is extended or adjusted under 35 U.S.C. 154(b) by 727 days.

(21) Appl. No.: 10/525,952

(22) PCT Filed: Aug. 26, 2003

(86) PCT No.: PCT/EP03/09438
§ 371 (c)(1),
(2), (4) Date: Oct. 17, 2005

(87) PCT Pub. No.: WO2004/025223
PCT Pub. Date: Mar. 25, 2004

(65) Prior Publication Data
US 2006/0155511 A1    Jul. 13, 2006

(30) Foreign Application Priority Data
Aug. 29, 2002 (DE) .................. 102 39 610

(51) Int. Cl.
*G06F 15/00* (2006.01)
(52) U.S. Cl. .......................................... 702/34
(58) Field of Classification Search .............. 702/33–35, 702/116, 122, 179–185; 73/1.02, 1.73; 324/509, 324/512, 537, 555–556
See application file for complete search history.

(56) References Cited

U.S. PATENT DOCUMENTS

| | | | |
|---|---|---|---|
| 4,532,013 A | 7/1985 | Dietz | |
| 4,638,658 A | 1/1987 | Otobe | |
| 4,953,386 A * | 9/1990 | Pearman et al. | 73/1.27 |
| 5,273,640 A | 12/1993 | Kusanagi | |
| 5,495,167 A * | 2/1996 | Cotroneo | 324/74 |
| 5,764,537 A * | 6/1998 | Walter et al. | 702/179 |
| 6,076,389 A | 6/2000 | Kaneko | |
| 6,510,397 B1 * | 1/2003 | Choe | 702/116 |
| 6,567,679 B1 * | 5/2003 | Khuri et al. | 600/345 |
| 6,772,082 B2 * | 8/2004 | van der Geest et al. | 702/116 |
| 6,856,930 B2 * | 2/2005 | Ammann | 702/116 |
| 6,975,967 B2 * | 12/2005 | Elwood et al. | 702/184 |

FOREIGN PATENT DOCUMENTS

| | | |
|---|---|---|
| DE | 42 21 848 A1 | 1/1994 |
| JP | 05209858 A | 8/1993 |
| WO | WO 02/054056 A1 | 7/2002 |

* cited by examiner

*Primary Examiner* — Tung S Lau
(74) *Attorney, Agent, or Firm* — Bacon & Thomas, PLLC

(57) ABSTRACT

A method for monitoring the functioning of sensors for the measurement and monitoring of state parameters of liquids or gases, especially in the field of process measurement technology, for example of electrochemical, electrophysical or optical sensors, wherein the sensor is placed into a test state at time intervals and test parameters are registered, or these test parameters are registered at time intervals in the course of the measured value registration. The registered parameters are stored and a backwards-looking, chronological development of the stored test parameters is evaluated for performing the functional monitoring and the development of sensor behavior to be expected in the future is predicted therefrom and information concerning the duration of the remaining, disturbance-free operation of the sensor is obtained.

26 Claims, 1 Drawing Sheet

METHOD FOR MONITORING SENSOR FUNCTION

FIELD OF THE INVENTION

The invention relates to a method for monitoring the functioning of sensors for the measuring and monitoring of state parameters of liquids or gases, especially in the field of process measurement technology. These can be any electrochemical, electrophysical or optical sensor, especially potentiometric or amperometric, photometric or spectrometric sensors. The state parameters can be, for example, the pH-value, the $CO_2$ or $O_2$ content, the concentration of a substance in an aqueous solution or the electrical conductivity.

BACKGROUND OF THE INVENTION

Sensors in the field of process measurement technology are subject to a strong application-related aging over time. Especially sensors used in liquid media, for instance for monitoring chemical processes. They are subjected to special demands, so that the requirements for their chemical and thermal resistance are high. Likewise, fouling and accretion formation on the sensor in the course of media contacts can interfere with its effectiveness and decrease its service life. The ability of a sensor to function and its service life are impaired, respectively influenced, by external factors or internal factors present in the sensor. It has, consequently, not been possible, to state, or predict, the service life of a sensor, neither in general, nor even for sensors in special cases of application. This situation is clearly disadvantageous.

In the case of electrochemical, electrophysical or optical sensors in the field of process measurement technology, calibrations are usually performed from time to time, wherein a two, or more, point calibration is established by means of appropriate standards. The calibration data obtained in this way are stored in a memory of a measured value transmitter or in the sensor itself (see the as yet unpublished DE 102 18 606.5) to be available for the measured value evaluation. During the registering and evaluation of a measured value, these calibration data, and perhaps other measured data, such as e.g. the temperature of the medium being measured, are then referenced.

For example, a pH-measurement chain, formed by a pH-glass-electrode and a reference-electrode, is characterized by the parameters zero-point and slope of the measurement chain voltage curve. Known glass electrode errors are slope error, alkali error and zero-point error. The service life of a pH-electrode is, consequently, dependent both on the conditions of use and on the durability of the electrode glass being used. As a rule, influences on the so-called membrane surface, thus accretions of lime, gypsum, fats, proteins and the like, can be removed by chemical cleaning. Not removable, however, are aging processes within the sensor, which occur even when the sensors are merely being stored. Above all, however, use at extreme pH-values or high temperatures decrease the service life of a glass electrode drastically.

Reference electrodes, in contrast, have a diaphragm as the site for the electrolytic contact between a reference electrolyte and the solution being measured. Errors can be caused, consequently, for example by fouling and blocking of the diaphragm or by so-called electrode poisoning due to intruding foreign ions in the reference electrolytes. The result is a changing of the cell voltage of the reference electrode (the half-cell voltage), of the so-called reference potential, which, in turn, shows up as a change in the zero point of the total measurement chain voltage.

There are, therefore, methods for monitoring the functioning of electrochemical sensors, wherein, for example, the internal resistance of a measuring electrode and a reference electrode is measured at timed intervals and, upon the exceeding or subceeding (falling beneath) of values determined in practice, an alarm is issued. According to this method, one waits until the sensor has reached a critical stage and must then be replaced.

There is a multitude of methods for monitoring the functioning of sensors in the field of process measurement technology, wherein the instantaneous successful functioning of sensors is checked, always on the basis of test parameters. DE 42 12 792 C2 and DE 34 19 034 are named by way of example.

SUMMARY OF THE INVENTION

An object of the present invention is to provide a method for monitoring the functioning of sensors for the measuring and monitoring of state parameters of liquids or gases, especially in the field of process measurement technology, for example, of electromechanical, eletrophysical or optical sensors, wherein the sensor is placed at time intervals in a test state and test parameters are registered, or test parameters are registered at time intervals during the course of registering measured values, such that it can be excluded that the sensor loses its ability to function during the subsequent operating period, until the next test of its functioning, and, indeed, without that the sensor is replaced long before reaching its wear limit, so that the useful service life of the sensor can be taken advantage of, to a maximum possible extent.

This object is achieved in the case of a generic method of the invention by storing the registered test parameters and, for executing the monitoring of the functioning, by evaluating a backward-looking, chronological development of the stored test parameters, and by, on the basis thereof, predicting the future development of the sensor behavior that is to be expected and winning information concerning the duration of the remaining, disturbance-free operation of the sensor.

The present invention is based on the discovery that, from the historical chronological development of test parameters obtained either in the context of the measured value registration or during periodic test states, especially during the calibration procedures, predictions into the future can be made concerning the development of the sensor behavior to be expected. Thus, the still remaining "wear reserve" can be determined. On the basis thereof, control procedures can be initiated or decisions concerning control procedures can be made, should such be desired.

At the same time, knowledge concerning the behavior of a certain sensor type, respectively a certain test parameter in the case of a specific sensor type, obtained via the invention can be used advantageously, for instance by using mathematical functions, which very accurately represent certain behavior based on experience, and by determining the parameters of such functions.

It would be at least fundamentally conceivable that a development over time according to the invention of a test parameter could be stored accessibly in the form of a curve or in some other manner for the monitoring of the functioning, so that, by comparison of the determined and stored test parameters of the sensor to be monitored with the stored data, conclusions can be reached concerning the development of the sensor behavior to be expected. A statement could, thus, especially be obtained on how long the sensor will still avoid a critical behavior, i.e. remain at a safe distance from a wear limit.—It turns out, however, to be advantageous, in contrast, when non-linear interpolation methods are used for the evaluating of the historical development over time of the stored test parameters, in order to obtain function parameters of a function describing the sensor behavior. Thus, by interpolation in the broadest sense, a function for the test parameters is established, whose values can then also be calculated for the future. Thus, in the broadest sense, an extrapolation of the test parameters determined in the past is done for the future.

As already indicated above, it turns out to be especially advantageous, when, for a certain sensor type and, if necessary, for a certain field of application of a certain sensor type, for instance in alkaline medium, a function resting on experience is provided and used, whose function parameters are then determined on the basis of a number of concrete, determined, test parameters. Preferably, polynomial functions are utilized for this.

When, as above, information concerning the duration of the remaining, disturbance-free operation of the sensor is discussed, this is to be understood in the broadest sense. Especially, following a particular determination of a test parameter, or at separated points in time, a first predictive value could be determined for a wear limit. At the wear limit, the sensor is still functional, i.e. it is in an operating state, which, by electrical compensating measures, (still) makes the functionality of the measuring device possible within, perhaps, narrower limits. On the other side of the wear limit, however, this is no longer the case. Thus, according to this further development of the invention, that point in time is determined, by calculation on the basis of the determined test parameters, especially on the basis of the function derived therefrom, or, in the broadest sense, by extrapolation, at which time the sensor will have reached the above-explained, wear limit.

According to a further embodiment of the invention, it could, however, also be tested, whether, before the next determining of test parameters, thus especially before the next calibration cycle, the wear limit will be reached. Depending on circumstances, a corresponding warning can be issued, or various other measures can be initiated, for instance automatic cleaning measures.

According to a further, advantageous variant of the method, it can be tested, whether a predictively won value of the test parameter lies within a warning range this side of the wear limit determined to this point in time. Also in this case, suitable information could be indicated, or measures initiated. The wear limit determined to this point in time can be corrected, especially on the basis of the predictively obtained value.

In an especially preferred, further development of the invention, it is provided that, on the basis of information obtained according to the invention concerning the duration of the remaining, disturbance-free operation, measures can be determined and issued and/or displayed and, perhaps, initiated, for maintenance, for example cleaning measures, replacement of the sensor liquid, of wear parts, or of filters or the like.

It proves, additionally, to be especially advantageous, when information concerning the duration of the remaining, disturbance-free operation is used to determine and, preferably, issue and/or display a predictive point in time for replacement of the sensor. This information concerning the preferred time for replacement of the sensor can, naturally, also be forwarded in any manner to central computing and control units and be processed there in any manner.

The above-discussed test parameters include any state data or condition information concerning the sensor, such as data or information which changes over the course of the operation of the sensor and exhibits a functional relationship to the service life of the sensor.

Especially in the case of potentiometric sensors, such as pH, O or CO sensors, it proves to be especially advantageous when the slope of the sensor signal, or signals (individual sensor, sensor chain, or sensor array), in a particular test state of the sensor, thus, for example, preferably during the cyclic calibration of the sensor, is registered and evaluated as the test parameter. Thus, for this route using the pH-sensor as an example, the slope of the measurement chain voltage, or cell-EMF, is used. Equally, it could involve the stored values of the calibration function of a photometric or spectrometric sensor.

Additionally, it has been found to be advantageous when the zero point of this measurement chain signal in a particular test state of the sensor is registered and evaluated as test parameter.

A special importance is also associated with the registering and evaluation of the internal resistance of an electrode as test parameter, since this is possible advantageously during normal measurement operation, while, in contrast, the determining of slope and zero point position is possible only during interruption of measurement operation, especially during the cyclically performed, calibration process.

However, also the change of the dynamic behavior of signals produced by the sensor itself can be registered and evaluated as test parameter. Thus, for example, the rise, respectively fall, time in the case of the signal registration, or the signal response time, or the dynamic behavior of the noise of the sensor, can be used according to the invention for the function monitoring. Dynamic behavior can be determined, for example, using a cyclovoltagram.

Additionally, it has been found to be advantageous, when, depending on sensor type, at least one (advantageously, however, more) different test parameter is registered cyclically. The information gained from each of these concerning the development of the sensor behavior to be expected and concerning the duration of the remaining, disturbance-free operation, can then be exploited such that, on the question of the reaching of the wear limit time point, those test parameters are considered, which indicate the closest wear limit time point.

It has also been found to be advantageous, when sensor-specific, basic data are utilized in the evaluation. On the basis of this sensor-specific, basic data, which can be obtained and used from a memory device of the sensor, of the measured value transmitter, or in some other manner, perhaps over the Internet or via update media, for example preferred and especially likewise stored functions can be won for the affected test parameters and utilized for performing the method.

In a further advantageous embodiment of the method of the invention, predictive suggestions regarding measures for maintenance or inspection, including detailed directions for cleaning the apparatus, replacing or testing, can be given, when it turns out that a value of a test parameter determined for the future lies in a warning zone this side of the wear limit. Likewise, recommendations for logistical measures, which relate to warehousing or ordering of material, can be issued based on appropriately stored experiential knowledge or be effected in any manner.

The results of the functional monitoring could, moreover, be transmitted to a process control location, for example, over process-compatible interfaces, such as Profibus, Foundation Fieldbus, Ethernet, and the like.

As means for the shared utilization of the identical user interface and for presenting the evaluated test parameters, for example in the measurement transmitter or an attached PC, an identical Device Type Manager (DTM) can, for example, be used.

BRIEF DESCRIPTION OF THE DRAWINGS

Further features, details and advantages of the invention will be apparent from the patent claims, the drawing and the description below of a preferred form of embodiment of the invention. The figures of the drawing show as follows:

DESCRIPTION OF THE PREFERRED EMBODIMENTS

Figure 1:
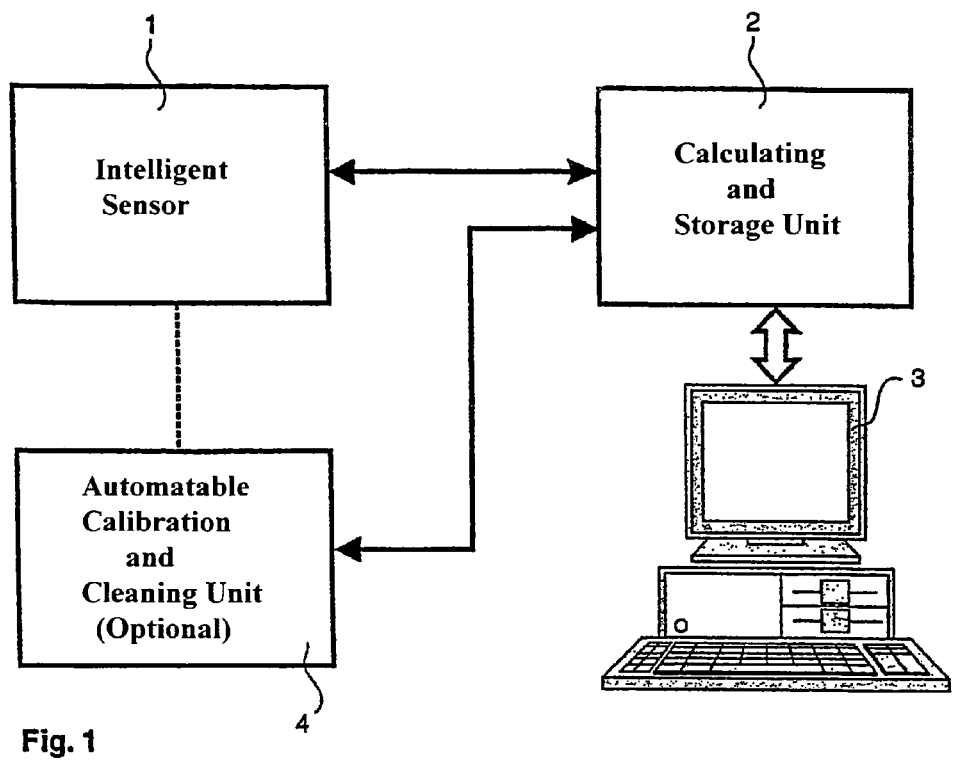
FIG. 1 is a schematic presentation of a part of a measuring setup.

FIG. 1 shows schematically a part of a measuring setup, including a sensor 1, a calculating and storage unit 2, and a display and operating unit 3. Integrated into the system as an optional component is an automatable calibration and cleaning unit 4.

Sensor 1 can be, advantageously, a sensor having a communications interface, an internal, digital memory, and associated, processor-controlled electronics; the method of the invention can, however, also be performed using a conventional sensor with analog signal output to the calculating unit 2 of a measured value transmitter.

Calculating and storage unit 2, and operating unit 3, can be integrated into a field device with graphic display; alternatively, however, a PC can be used, as shown. The measuring setup also possesses a communications interface, in order to be able to connect with a central process control location over the established communication methods via the Internet or local intranet, or to be contacted from the outside.

Figure 2:
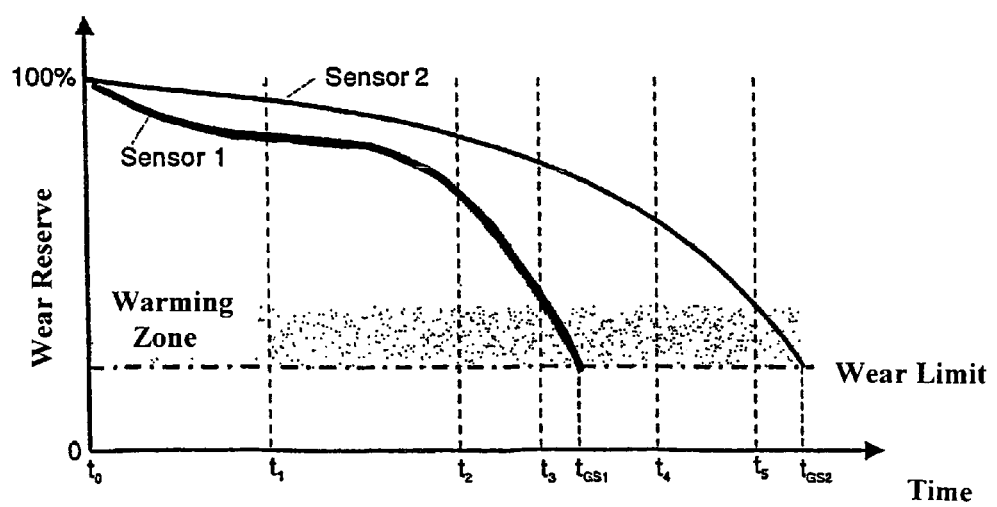
FIG. 2 is a plot of sensor-specific test parameters over time.

FIG. 2 is a plot of sensor-specific data of sensor-specific test parameters as a function of time. For example, as a result of external influences, the ability of the sensor to function is limited with respect to time; it is subject to wear. Sensor specifically, there are various influencing variables, such as exposure to the medium being measured, exposure to temperature and climatic influences, and also age-related wear, as well as other chemical or physical processes, which bring about, at different rates, a depletion of the so-called wear reserve down to the defined wear limit.

For a particular test parameter, a parameter value corresponding to the wear limit is stored in the storage unit as a function of specific sensor type. Likewise defined and stored is a warning region bordering thereon. As indicated above, upon reaching the wear limit, the measurement setup can, it is true, still function, but a further change or worsening of the sensor parameter would lead to a malfunction.

For the example of a pH measuring chain, FIG. 2 shows a plot of the so-called electrode slope of the measurement chain voltage. The measurement setup registers to this end the measurement chain voltages during a given calibration process and normalizes the obtained values in manner known per se (for example as described in DIN IEC 746-2). The results are then stored in the storage unit.

Via a so-called predictive program for the slope monitoring, when a first number of values are present, a polynomial function is determined by non-linear interpolation, and a first predictive value for the future wear limit is determined. This is stored. Depending on the conditions of use and the calibration cycles resulting therefrom, which can occur with separations of days or weeks, the data are supplemented, i.e. further test parameters are registered and their polynomial functions determined and, in each case, the values of the functions are determined at further times $t_i$ by extrapolation in the broadest sense. As soon as the relevant test parameter sinks to the defined value of the warning range, for example the electrode slope value sinks to 80% of the theoretical slope of the measurement chain voltage over the H+ ion concentration, the also determined wear limit time point is issued as warning information. In the examples of the two sensors of FIG. 2, these are the times $t_{GS1}$ and $t_{GS2}$.

As mentioned above, the measuring chain voltage zero point or the internal resistance of the glass electrode and/or the reference electrode can be considered alternatively or additionally as test or monitoring parameters.

The tactic, according to the invention, of considering the previous development of test parameters registered at points separated in time, for determining the development of sensor behavior to be expected in the future, leads to an optimum utilization of the functional capability of the sensor. The sensor does not have to be replaced earlier than its service life, while the risk is largely minimized that the sensor will become unable to function during its intended operation.

Equally, predictive precautionary measures, e.g. providing and procuring of replacement materials in the sense of an optical maintenance strategy, can be initiated.

The invention claimed is:

1. A method for monitoring the functioning of a sensor which measures and monitors a state parameter of liquids or gases, comprising the steps of:
   placing the sensor in a test state at time intervals;
   registering test parameters at time intervals or at time intervals during the course of registering measured values;
   storing the registered test parameters;
   evaluating a backward-looking chronological development of the stored test parameters in order to perform functional monitoring by using an non-linear interpolation method for evaluating the historical development over time of the stored test parameters in order to obtain function parameters of a function describing the sensor behavior;
   predicting from said evaluations the development of sensor behavior to be expected in the future; and
   obtaining thereby, by a processor, information concerning the duration of the remaining disturbance-free operation of the sensor,
   wherein the sensor is a potentiometric, amperometric, photometric, or spectrometric sensor.

2. The method as defined in claim 1, wherein:
   a function is specified and used for said sensor, which reproduces the experience-based behavior of the particular sensor.

3. The method as defined in claim 1, further comprising the step of:
   testing whether the wear limit of the sensor will be reached before the next registering of test parameters and correspondingly issuing a corresponding warning or correspondingly initiating automatic cleaning measures.

4. The method as defined in claim 1, further comprising the step of:
   determining and issuing displaying or initiating measures for maintenance on the basis of the information concerning the duration of the remaining, disturbance-free operation.

5. The method as defined in claim 1, wherein:
   as a test parameter, the slope of the sensor signal, or signals is registered and evaluated.

6. The method as defined in claim 1, wherein:
as a test parameter, the zero point of the sensor signal, or signals is registered and evaluated.

7. The method as defined in claim 1, wherein:
as a test parameter, the internal resistance of an electrode is registered and evaluated.

8. The method as defined in claim 1, wherein:
as a test parameter, the change of the dynamic behavior of signals produced by the sensor itself is registered and evaluated.

9. The method as defined in claim 1, wherein:
a plurality of different test parameters are registered and evaluated.

10. The method as defined in claim 1, further comprising the step of:
obtaining a sensor specific, basic data from a storage arrangement of the sensor or the measured value transmitter over the internet or over update media, for the evaluation.

11. The method as defined in claim 1, comprising a further step of:
determining and issuing or displaying a predictive point in time for replacement of the sensor, of a sensor liquid, or of wear parts of the sensor.

12. The method as defined in claim 1, wherein:
at least one or several of said steps are performed in a measuring setup comprising a sensor, a calculating and storage unit and a display and operating unit.

13. The method as defined in claim 2, wherein: the function involves a polynomial function.

14. The method as defined in claim 5, wherein:
the sensor is a pH-sensor and the test parameter is the slope of the measurement chain voltage.

15. The method as defined in claim 5, wherein:
the slope of the sensor signal or signals is registered during interruption of measurement operation of the sensor during a calibration process.

16. The method as defined in claim 6, wherein:
the zero point of the sensor signal, or signals is registered during interruption of measurement operation of the sensor during a calibration process.

17. The method as defined in claim 7, wherein:
said electrode is a glass electrode or a reference electrode.

18. A measuring setup, comprising:
a sensor adapted to measure and monitor state parameters of liquids or gases, the sensor comprising a signal output;
a calculating and storage unit, adapted to receive signals from said sensor; and
a display and operating unit connected to the calculating and storage unit;
wherein
said measuring setup is adapted to:
register and store test parameters at time intervals;
evaluating a backward-looking chronological development of the stored test parameters in order to perform functional monitoring by using a non-linear interpolation method for evaluating the historical development over time of the stored test parameters in order to obtain function parameters of a function describing the sensor behavior;
predicting from said evaluations the development of the sensor behavior to be expected in the future, and obtaining thereby information concerning the duration of the remaining disturbance-free operation of said sensor; and
determining by a processor a predictive point in time for replacement of the sensor,
wherein the sensor is a potentiometric, amperometric, photometric, or spectrometric sensor.

19. The measuring setup as defined in claim 18, wherein:
the measuring setup is further adapted to testing whether the wear limit of the sensor will be reached before the next registering of test parameters and correspondingly issuing a corresponding warning or correspondingly initiating automatic cleaning measures.

20. The measuring setup as defined in claim 18, wherein:
the measuring setup is adapted to determining and issuing or displaying a predictive point in time for replacement of the sensor, of a sensor liquid, or of wear parts of the sensor.

21. A method for monitoring the functioning of a sensor which measures and monitors a state parameter of liquids or gases, comprising the steps of:
placing the sensor in a test state at time intervals;
registering test parameters at time intervals or at time intervals during the course of registering measured values;
storing the registered test parameters;
evaluating a backward-looking chronological development of the stored test parameters in order to perform functional monitoring by using a non-linear interpolation method for evaluating the historical development over time of the stored test parameters in order to obtain function parameters of a function describing the sensor behavior;
predicting from said evaluations the development of sensor behavior to be expected in the future; and
obtaining thereby, by a processor, information concerning the duration of the remaining disturbance-free operation of the sensor, based on said information determining and issuing or displaying a predictive point in time for replacement of the sensor, a sensor liquid, or of wear parts of the sensor,
wherein the sensor is a potentiometric, amperometric, photometric, or spectrometric sensor.

22. The method as defined in claim 21, wherein:
at least one or several of said steps are performed in a measuring setup comprising a sensor, a calculating and storage unit and a display and operating unit.

23. The method as defined in claim 21, wherein:
the sensor is a pH-sensor and the test parameter is the slope of the measurement chain voltage.

24. The method as defined in claim 21, wherein:
as a test parameter the zero point of the sensor signal, or signals is registered and evaluated.

25. The method as defined in claim 21, wherein:
as a test parameter, the internal resistance of an electrode is registered and evaluated.

26. The method as defined in claim 21, wherein:
as a test parameter, the change of the dynamic behavior of signals produced by the sensor itself is registered and evaluated.

* * * * *